US00PP19461P3

(12) United States Plant Patent
Jensen

(10) Patent No.: US PP19,461 P3
(45) Date of Patent: Nov. 18, 2008

(54) *CAMPANULA* PLANT NAMED 'PKMT02'

(50) Latin Name: ***Campanula* sp.**
Varietal Denomination: PKMT02

(75) Inventor: Gert Kim Jensen, Norge (DK)

(73) Assignee: Gartneriet PKM A/S, Odense N (DK)

( * ) Notice: Subject to any disclaimer, the term of this patent is extended or adjusted under 35 U.S.C. 154(b) by 0 days.

(21) Appl. No.: 11/811,058

(22) Filed: Jun. 8, 2007

(65) Prior Publication Data

US 2008/0189819 P1 Aug. 7, 2008

(51) Int. Cl.
*A01H 5/00* (2006.01)

(52) U.S. Cl. ..... Plt./414
(58) Field of Classification Search ..... Plt./414
See application file for complete search history.

(56) References Cited

PUBLICATIONS

Print–out application No. and filing date from Canadian Food Inspection Agency—Plant Breeder's Right Office (CPVO) website (www.inspection.gc.ca) for corresponding, Canadian PBR application No. 07–5889 filed Apr. 20, 2007.

Japanese Plant Breed's Rights Application 20999 filed Apr. 25, 2007.

*Primary Examiner*—Annette H Para
(74) *Attorney, Agent, or Firm*—Foley & Lardner LLP

(57) ABSTRACT

A new and distinct cultivar of *Campanula* plant named 'PKMT02', characterized by having upright, compact plant habit with a wide spread area; dense and bushy plant form, mainly due to short, upright and stiff stems; vigorous growth habit, but with less need for chemical growth retardation; higher number of flowers per plant; and dark violet flower color.

3 Drawing Sheets

Latin name of genus and species of the plant claimed: *Campanula* sp.
Variety denomination: 'PKMT02'.

BACKGROUND OF THE INVENTION

The present invention relates to a new and distinct cultivar of *Campanula* plant, botanically known as *Campanula* sp., commonly known as Bellflower, and hereinafter referred to by the name 'PKMT02'.

The new *Campanula* 'PKMT02' is a product of a planned breeding program conducted by the inventor, Gert K. Jensen, in Søhus, Denmark. The objective of the breeding program is to develop a new *Campanula* cultivar with compact plant form and dark violet flowers.

The new *Campanula* cultivar originated from a cross made in a controlled breeding program by the inventor in 2004 in Søhus, Denmark. The female or seed parent is a *Campanula tubulosa* cultivar 'PKMT01' (patented, described in U.S. Plant Pat. No. 17,226). The male or pollen parent is the unpatented wild form of *Campanula carpatha*. The new *Campanula* 'PKMT02' was discovered and selected by the inventor as a single flowering plant within the progeny of the stated cross in January of 2004 in a controlled environment in Søhus, Denmark. The inventor selected 'PKMT02' on the basis of its compact plant form, dark violet colors and freely flowering habit. Plants of 'PKMT02' are more upright, compact and freely flowering than plants of the original parental cultivars.

Asexual reproduction of the new *Campanula* cultivar by terminal cuttings was first performed in September of 2004 in Søhus, Denmark, and has demonstrated that the combination of characteristics as herein disclosed for the new cultivar are firmly fixed and retained through successive generations of asexual reproduction.

SUMMARY OF THE INVENTION

The following traits have been repeatedly observed and are determined to be the unique characteristics of 'PKMT02'. These characteristics in combination distinguish 'PKMT02' as a new and distinct cultivar:

1. Upright, compact plant habit with a wide spread area;
2. Dense and bushy plant form, mainly due to short, upright and stiff stems;
3. Vigorous growth habit, but with less need for chemical growth retardation;
4. Higher number of flowers per plant; and
5. Dark violet flower color.

Side-by-side comparisons were conducted by the inventor in Søhus, Denmark, between plants of the new *Campanula* sp. 'PKMT02' and plants of the *Campanula carpatha* wild type. Plants of 'PKMT02' differ from plants of *Campanula carpatha* wild type in the following characteristics:

1. Plants of 'PKMT02' have large, dark violet, upright, single and campanulate flowers;
2. Plants of 'PKMT02' have shorter internodes, petioles, and leaves;
3. Plants of 'PKMT02' have more upright growth;
4. Plants of 'PKMT02' have shorter peduncles;
5. Plants of 'PKMT02' are shorter and more compact in shape; and
6. Plants of 'PKMT02' produce more flowers per plant.

The most similar comparison cultivar to the new *Campanula* sp. 'PKMT02' is the female parental cultivar, *Campanula tubulosa* 'PKMT01' (patented, described in U.S. Plant Pat. No. 17,226). Plants of the new *Campanula* sp. 'PKMT02' differ from plants of *Campanula tubulosa* 'PKMT01' in the following characteristics:

1. Plants of 'PKMT02' have more spread (25 cm) than plants of 'PKMT01' (20 cm);
2. Plants of 'PKMT02' have less lateral branches (about 16) which are longer (10–13 cm) and yellow-green in color (RHS 146D) than plants of 'PKMT01' (about 25 lateral branches which are 3–4 cm in length and green in color, RHS 138A);
3. Plants of 'PKMT02' have taller inflorescence height (9–11 cm) than plants of 'PKMT01' (about 5–8 cm); and
4. Plants of 'PKMT02' produce less flowers and buds per plant (150–250) than plants of 'PKMT01' (300–400);
5. Plants of 'PKMT02' have buds with yellow-green color (RHS 149D) whereas plants of 'PKMT01' have buds with green-white color (RHS 157A); and
6. Plants of 'PKMT02' produce dark violet flowers (RHS 87A) whereas plants of 'PKMT01' produce violet flowers (RHS 84A).
7. Plants of 'PKMT02' produce yellow-orange anthers and pollen (RHS 16C), green-yellow styles (RHS 1D), and a yellow-green ovaries (RHS N144C) whereas plants of 'PKMT01' produce yellow-white anthers and pollen (RHS 158B) and white styles and ovaries (RHS 155D).

BRIEF DESCRIPTION OF THE PHOTOGRAPHS

The accompanying colored photographs illustrate the overall appearance of the new *Campanula* 'PKMT02', showing the colors as true as it is reasonably possible to obtain in colored reproductions of this type. Colors in the photographs may differ slightly from the color values cited in the detailed botanical description, which more accurately describe the actual colors of 'PKMT02'.

DETAILED BOTANICAL DESCRIPTION

Figure 1:
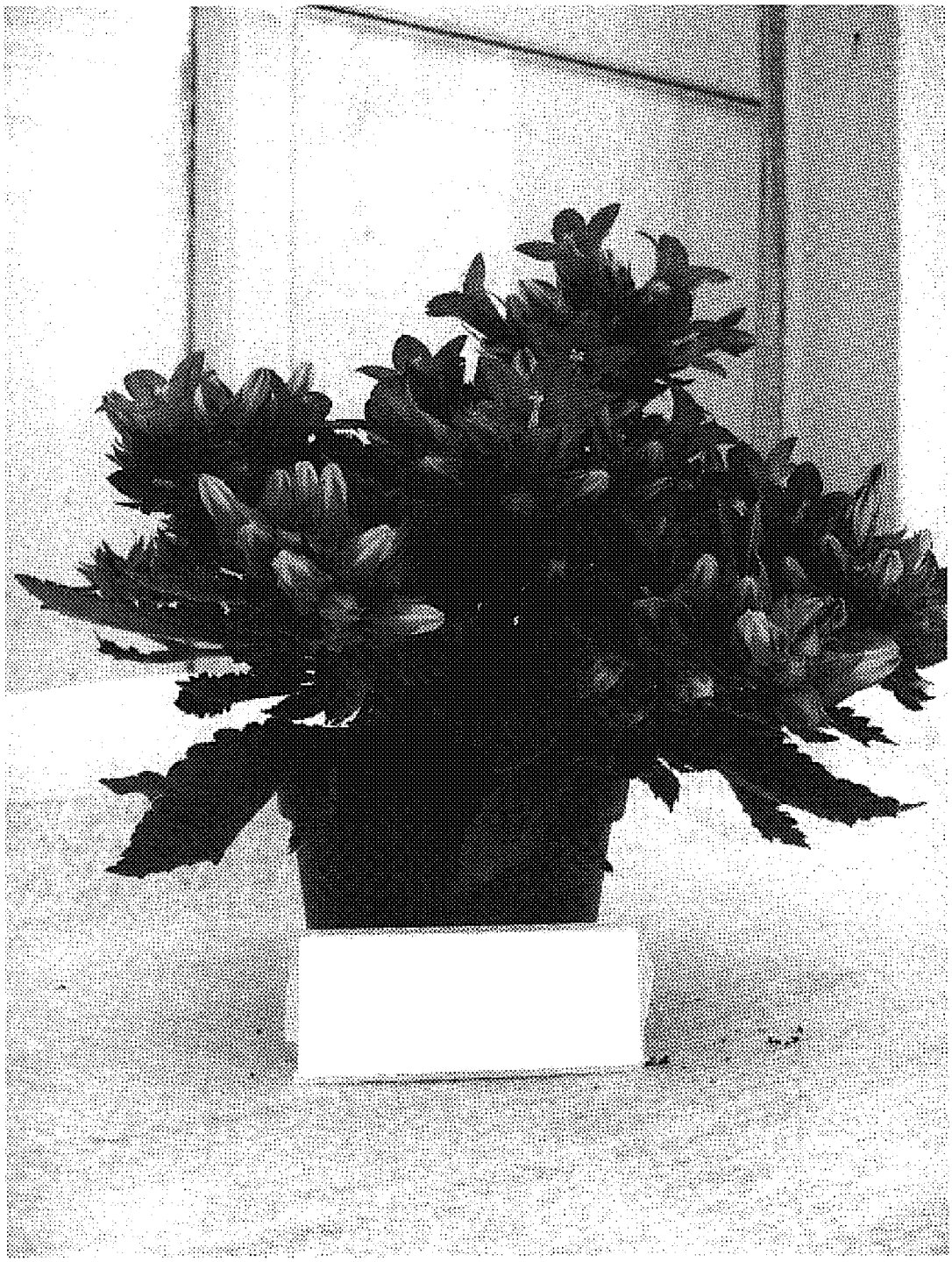
FIG. 1 shows a side perspective view of a typical flowering plant of 'PKMT02', as grown in a 10.5 cm pot at 14 weeks of age.
Figure 2:
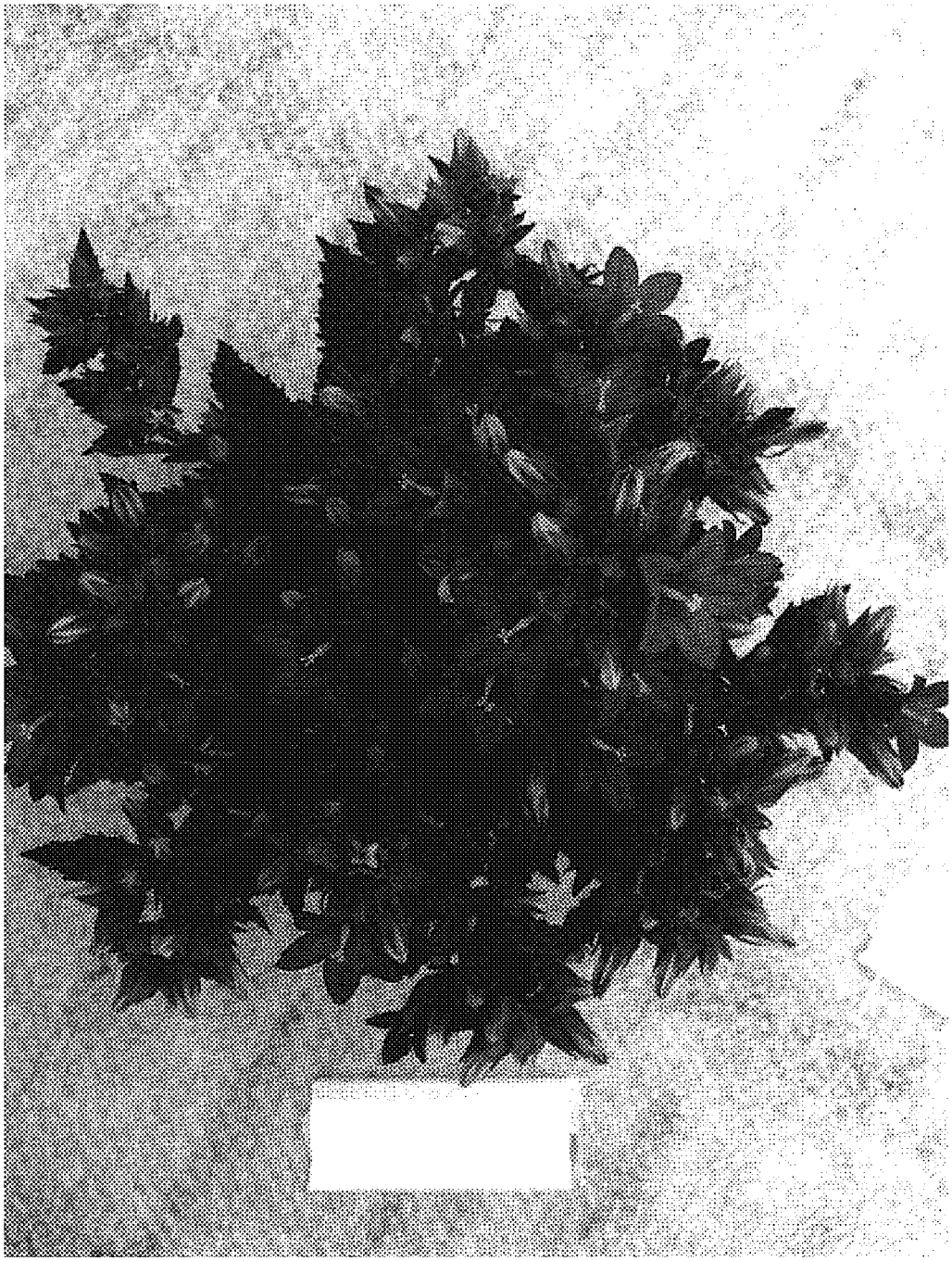
FIG. 2 shows a top perspective view of a typical flowering plant of 'PKMT02', as grown in a 10.5 cm pot at 14 weeks of age.
Figure 3:
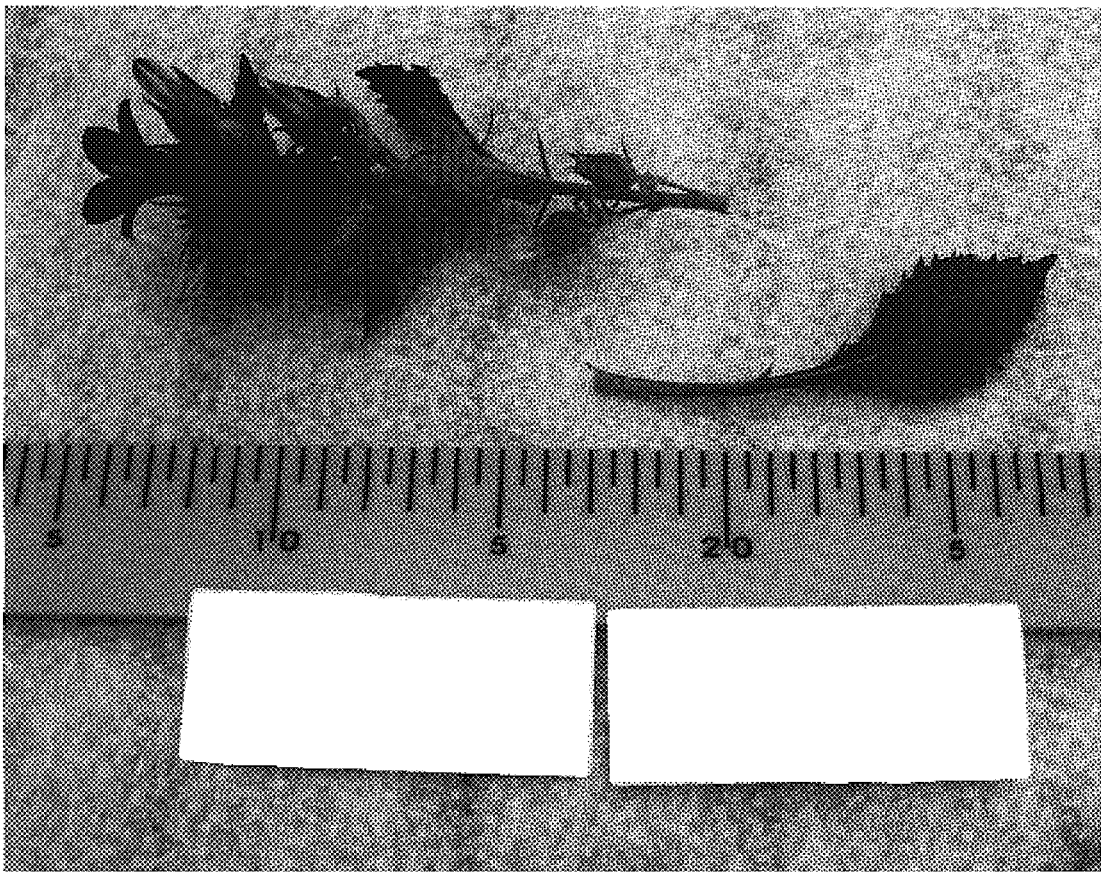
FIG. 3 show a close-up view of typical flowering raceme and leaves of 'PKMT02' at 14 weeks of age.

The new *Campanula* 'PKMT02' has not been observed under all possible environmental conditions. The phenotype of the new cultivar may vary significantly with variations in environment such as temperature, light intensity, day length, and fertility level without any variance in genotype.

The aforementioned photographs, together with the following observations, measurements and values describe plants of the new *Campanula* 'PKMT02' as grown in a heated and lighted, glass-covered greenhouse in Søhus, Denmark, under conditions which closely approximate those generally used in commercial practice where day temperatures in the greenhouse range from 18–20° C. and the night temperature range from 16–18° C. Ambient light levels used while growing plants of 'PKMT02' are +90 $Wm^2$. Plants of 'PKMT02' are grown with 18 hour long day photoperiodic treatments. No growth retardants used.

The age of the 'PKMT02' plants described is 18 weeks old and grown in 10.5 cm pots. The photographs and descriptions were taken during the winter season when day temperatures in glass-covered greenhouse range from 18–20° C. and when night average temperatures in glass-covered greenhouse range from 16–18° C.

Color references are made to The Royal Horticultural Society Colour Chart (R.H.S.), $4^{th}$ edition, except where general colors of ordinary significance are used.

Classification:
- *Botanical.*—*Campanula* sp.

Parentage:
- *Female or seed parent.*—*Campanula tubulosa* cultivar designated 'PKMT01' (patented, described in U.S. Plant Pat. No. 17,226).
- *Male or pollen parent.*—Unpatented wild form of *Campanula carpatha.*

Propagation:
- *Type cutting.*—Terminal vegetative cuttings.
- *Time to initiate roots.*—About 12 to 15 days at 18 to 21° C. in tunnels in a greenhouse.
- *Root description.*—Fine, well branched.

Plant description:
- *Form.*—Biennial, herbaceous plant with upright, compact plant habit. Produced as a potted plant. Campanulate flowers in racemes. Freely branching with lateral branches forming at every node.
- *Crop time.*—After rooting, about 18 weeks are required to produce finished flowering plants in 10.5 cm pots.
- *Vigor.*—Vigorous growth rate.
- *Plant height* (*from pot rim to top of plant plane*).—About 14 to 16 cm.
- *Plant spread* (*width*).—About 25 cm.
- *Lateral branches.*—Habit: Freely branching. Quantity: About 16 per plant. Leaves per Lateral Branch: About 8. Length: 10 cm to 13 cm. Diameter: About 2 mm to 4 mm. Internode Length: 1.5 cm to 2.0 cm.
- *Stem.*—Shape: Round. Strength: Strong. Aspect: Upright and outward. Texture: Hirsute and white lactate. Color: RHS 146D, yellow-green.

Foliage description:
- *Arrangement.*—Alternate, single.
- *Overall shape.*—Oblanceolate.
- *Apex shape.*—Acute.
- *Base shape.*—Cuneate.
- *Length.*—About 20 mm to 90 mm.
- *Width.*—About 10 mm to 20 mm.
- *Margin.*—Serrate.
- *Texture* (*both sides*).—Hirsute.
- *Color* (*mature and immature*).—Upper surface: RHS 137A, green; Lower Surface: RHS 137C, green.
- *Venation.*—Pattern: Reticulate, partly net-veined. Color: Upper surface: RHS 137A, green; Lower Surface: RHS 137C, green.
- *Petiole.*—Length: Up to 3.0 cm. Diameter: 4×2 mm, flat-winged. Color: RHS 144D, yellow-green.

Inflorescence description:
- *Flower arrangement and shape.*—Single, upright to outward, large acropetal campanulate flowers in compressed raceme with large calyx.
- *Natural flowering season.*—Continuous throughout the spring and summer. Season can be extended year round by long day treatments.
- *Time to flower.*—About 8 weeks.
- *Rate of opening.*—About 30 flowers per week.
- *Flower longevity.*—On the plant, flowers last about 5 to 9 days; however, longevity of individual flowers is highly dependent on temperature and light conditions. Flowers persistent.

*Fragrance.*—Yes, fresh, chilly scent.

*Inflorescence size.*—Height: 9 cm to 11 cm. Diameter: 4 to 7 cm.

*Number of flowers per inflorescence.*—5 to 11.

*Number of flowers per lateral stem.*—About 20 to 30.

*Number of flowers and buds per plant.*—About 150 to 250.

*Buds.*—Length: Up to 18 mm. Diameter: Up to 5 mm. Shape: Oblong, star-shaped cross section. Color: RHS 149D, yellow-green.

*Flowers.*—Aspect: Upward to outward. Shape: Deltoid, cuspidate petal lobes. Depth (height): About 25 mm. Diameter: About 25 to 30 mm. Flowering: Persistent. Corolla color: Upper surface: RHS 87A; Throat: RHS N87D; Underside: RHS 84A. Calyx: Double with pointed tips (mucronulate), reflexed bracts, green color RHS 137C to RHS 138B.

*Petals.*—Arrangement: Sympetalous. Quantity per flower: About 4 to 5. Length: About 8 to 10 mm. Width: About 8 to 10 mm. Overall Shape: Deltoid. Tip: Cuspidate. Base: Fused. Margin: Entire. Texture: Silky. Color (when opening); Upper surface: Violet, RHS N87A; Under surface: Violet, RHS 84A. Color (when fully opened): Upper surface: Violet, RHS N87B, with throat color of RHS N87D; Under surface: Violet, RHS 88C. Fading: Fading to violet, RHS N87B.

*Sepals.*—Arrangement: Basally fused. Appearance: Hirsute. Quantity per flower: 5 lobes, 5 bracts. Length: About 11 mm to 12 mm. Width: About 5 to 6 mm. Overall shape: Mucronate. Tip: Mucronate. Base: Fused to bracts. Bracts shape: Folded, round, reflexed. Margin: Entire. Texture: Hirsute. Color (immature): Upper and under surfaces: Green, RHS 138C to RHS 138D. Color (mature): Upper and under surfaces: Green, RHS 137C.

*Peduncles.*—Length: About 4 mm to 6 mm. Diameter: About 1 mm. Angle: Varies. Strength: Strong. Color: Yellow-green, RHS 146D.

Reproductive organs:

*Androecium.*—Stamen: Quantity: 3 to 5, linear anthers initially fused. Anther: Shape: Lanceolate. Length: About 6 to 7 mm. Color: Yellow-orange, RHS 16C. Pollen: Amount: Plenty. Color: Yellow-orange, RHS 16C.

*Gynoecium.*—Pistil: Quantity: 1. Length: About 25 mm to 30 mm. Stigma: Shape: Pentapartite. Color: Green-yellow, RHS 1B. Style: Length: About 20–22 mm. Color: Green-yellow, RHS 1D. Ovary: Color: Yellow-green, RHS 144C.

Seed/fruit: None observed.

Weather tolerance: Plants of the new *Campanula* have exhibited good tolerance to drought, rain and wind, with low temperature resistance to 0° C.

Disease/pest resistance: 'PKMT02' has not been tested.

Disease/pest susceptibility: 'PKMT02' has not been tested.

I claim:

1. A new and distinct cultivar of *Campanula* plant named 'PKMT02', as illustrated and described herein.

* * * * *